(12) United States Patent
Hines

(10) Patent No.: US 9,763,810 B2
(45) Date of Patent: Sep. 19, 2017

(54) HYDRAULICALLY AMPLIFIED VACUUM PUMP FOR PROSTHETIC AND ORTHOTIC DEVICES

(71) Applicant: Otto Bock HealthCare LP, Minneapolis, MN (US)

(72) Inventor: Peter H. Hines, Salt Lake City, UT (US)

(73) Assignee: OTTO BOCK HEALTHCARE LP, Minneapolis, MN (US)

( * ) Notice: Subject to any disclaimer, the term of this patent is extended or adjusted under 35 U.S.C. 154(b) by 46 days.

(21) Appl. No.: 14/469,448

(22) Filed: Aug. 26, 2014

(65) Prior Publication Data

US 2016/0058583 A1 Mar. 3, 2016

(51) Int. Cl.
| | |
|---|---|
| *A61F 2/80* | (2006.01) |
| *A61F 2/68* | (2006.01) |
| *A61F 2/74* | (2006.01) |
| *A61F 2/50* | (2006.01) |
| *A61F 2/60* | (2006.01) |

(52) U.S. Cl.
CPC ............... *A61F 2/80* (2013.01); *A61F 2/68* (2013.01); *A61F 2/60* (2013.01); *A61F 2002/5006* (2013.01); *A61F 2002/5072* (2013.01); *A61F 2002/5084* (2013.01); *A61F 2002/742* (2013.01); *A61F 2002/745* (2013.01); *A61F 2002/747* (2013.01); *A61F 2002/748* (2013.01); *A61F 2002/802* (2013.01); *A61F 2002/805* (2013.01); *A61F 2002/807* (2013.01)

(58) Field of Classification Search
CPC .. A61F 2/80; A61F 2002/74–2002/748; A61F 2002/802–2002/807
See application file for complete search history.

(56) References Cited

U.S. PATENT DOCUMENTS

| | | | |
|---|---|---|---|
| 2,657,393 A * | 11/1953 | Haller | A61F 2/60 188/317 |
| 6,645,253 B2 | 11/2003 | Caspers | |
| 6,761,742 B2 | 7/2004 | Caspers | |
| 7,025,792 B2 | 4/2006 | Collier | |
| 7,744,653 B2 | 6/2010 | Rush et al. | |
| 8,007,543 B2 | 8/2011 | Martin | |
| 8,568,489 B2 | 10/2013 | Finlinson et al. | |
| 2010/0312360 A1 | 12/2010 | Caspers | |
| 2012/0123559 A1 | 5/2012 | Mosler et al. | |

(Continued)

*Primary Examiner* — Marcia Watkins
(74) *Attorney, Agent, or Firm* — Holland & Hart

(57) ABSTRACT

Methods and apparatus are disclosed relating to a mechanical vacuum socket pump used to establish a vacuum in a socket of an artificial limb. In one case, the pump includes a housing within which two pistons coaxially reciprocate. A surface of each of the pistons is linked hydraulically, such that driving one piston causes movement of the other piston through a hydraulic chamber. One piston is also linked to a pneumatic chamber such that movement of that piston draws air from a limb socket or expels air to the atmosphere upon movement of the piston's pneumatic surface. The surface area of the hydraulic surface of this piston is significantly less than the surface area of the pneumatic surface, so a small volumetric displacement of hydraulic fluid may cause a large displacement of air. Thus, the pump efficiently pumps air with minimal compression and extension of the pump as a whole.

21 Claims, 8 Drawing Sheets

(56) References Cited

U.S. PATENT DOCUMENTS

| | | |
|---|---|---|
| 2012/0173000 A1 | 7/2012 | Caspers |
| 2012/0173001 A1 | 7/2012 | Caspers |
| 2013/0096694 A1 | 4/2013 | Caldwell |
| 2013/0211544 A1 | 8/2013 | Jonsson et al. |
| 2013/0289741 A1 | 10/2013 | Halldorsson et al. |
| 2013/0289742 A1 | 10/2013 | Halldorsson et al. |

* cited by examiner

HYDRAULICALLY AMPLIFIED VACUUM PUMP FOR PROSTHETIC AND ORTHOTIC DEVICES

TECHNICAL FIELD

The present disclosure generally relates to prosthetic and orthotic devices and specifically relates to a dynamic, hydraulically activated vacuum pump for sockets in prosthetic and orthotic devices.

BACKGROUND

An amputee is a person who has lost part of an extremity or limb such as a leg or arm which commonly may be termed as a residual limb. Residual limbs come in various sizes and shapes with respect to the stump. That is, most new amputations are either slightly bulbous or cylindrical in shape while older amputations which may have had significant atrophy are generally more conical in shape. Residual limbs may further be characterized by their various individual problems or configurations including the volume and shape of a stump and possible scar, skin graft, bony prominence, uneven limb volume, neuroma, pain, edema or soft tissue configurations.

Prosthetic and orthotic devices provide mobility and functionality to amputees, but must be secured to a residual limb to do so. Many devices include sockets configured for reception of the residual limb. Because the size and shape of a residual limb may vary among amputees, and even for one amputee over days or years of prosthetic wear, creating vacuum between the surface of the residual limb (or a sock, elastomeric liner, or sheath covering the limb) and the socket to keep the prosthetic device from loosening or disconnecting from the stump is beneficial for an amputee.

The use of vacuum to attach an artificial limb to a residual limb (i.e., vacuum suspension) offers many advantages over more traditional means of artificial limb retention such as straps, retaining pins attached to a liner covering the limb, and suction type sockets which do not use a vacuum pump. When the entire socket/limb interface is subject to high levels of vacuum, the benefits include exceptional retention with no detectable movement between the residual and artificial limbs, residual limb volume management, increased proprioception, and improved circulation accompanied by a reported increased rate of wound healing on the residual limb.

Both electric and mechanical vacuum pumps are available for prosthetic use. The most common designs implement a moving wall to generate vacuum. Electric pumps typically employ a diaphragm-like moving wall which is driven up and away from a surface. As the diaphragm is pulled away from the surface air is pulled into a vacuum chamber created between the surface and the diaphragm. An electric pump may advantageously consume none of the available space between the socket and the foot, and they are also always "on," so the vacuum level does not rely on walking or other movement by an amputee and will not drop below a selected level unless a leak occurs which exceeds the capacity of the pump or the battery of the pump is depleted. However, they may have batteries to recharge, are susceptible to impact damage, and may be difficult to position on the limb.

Mechanical pumps, on the other hand, are weight-activated rather than electrically powered. Mechanical pumps are also durable and have a high resistance to impact forces. A mechanical pump does not require recharging and can incorporate additional prosthetic functions, such as vertical shock absorption and rotation, at the cost of taking up available space between the socket and the end of the limb. Tall foot designs are typically more comfortable and natural-feeling for the amputee than shorter foot designs, but the length of the mechanical pump reduces the height available for a prosthetic foot or other components for the limb. Furthermore, if the pump has large vertical deflection between extension and compression, the amputee's gait may be negatively unbalanced.

Additionally, none of the benefits of vacuum suspension exist until significant vacuum is created since the socket will not be firmly connected to the residual limb. This means an amputee using a mechanical pump as part of a vacuum-retained artificial limb must cycle the pump repeatedly to create vacuum before attempting to use the artificial limb, whether after donning the limb or after intentionally releasing the vacuum. This may be frustrating and time consuming. Vacuum limbs also have various potential leak sources and vacuum will often bleed off after a period of inactivity. Therefore, there is a need for improvements in vacuum suspended artificial limbs and orthotics.

SUMMARY

One aspect of the present disclosure relates to a vacuum socket pump apparatus for an artificial limb. The pump apparatus may comprise a housing having a socket connection portion and a prosthetic limb connection portion, wherein the socket connection portion is adapted to connect to a limb socket and the prosthetic limb connection portion is adapted to connect to a prosthetic limb portion. The pump apparatus may also include a first piston configured to reciprocate within the housing and a second piston configured to reciprocate within the first piston upon displacement of the first piston relative to the housing, with the second piston having a pneumatic surface. The second piston and the housing may form a pneumatic chamber between an interior surface of the housing and the pneumatic surface, wherein the pneumatic chamber may be configured to receive air from the socket upon expansion of the pneumatic chamber and to evacuate air from the pump apparatus upon compression of the pneumatic chamber. Displacement of the first piston relative to the housing may hydraulically produce a greater displacement of the second piston relative to the housing.

In some embodiments, the first piston has a first hydraulic surface and the second piston has a second hydraulic surface, and the first hydraulic surface has a greater surface area than the second hydraulic surface. Here, the pneumatic surface may have a greater surface area than the second hydraulic surface.

The second piston may be biased away from the first piston by an biasing member, such as a spring element or elastic element. The pump may also include an intake valve and an exhaust valve, wherein the intake valve may provide one-way displacement of air from a limb socket into the pneumatic chamber, and the exhaust valve may provide one-way displacement of air out of the pneumatic chamber.

In some cases, the vacuum pump apparatus may comprise a pyramid connector interface to connect to a socket or to a prosthetic limb portion. Thus, the artificial limb may be part of, or entirely, an artificial leg. The vacuum pump apparatus may be positioned in a shin portion of the artificial leg or in a femoral portion of the artificial leg.

In an example embodiment, a length of displacement of the first piston relative to the housing between a fully extended position and a fully compressed position may be about 10 millimeters or less. Displacement of the first piston relative to the housing may displace a hydraulic fluid that hydraulically displaces the second piston relative to the housing.

Another aspect of the present disclosure relates to a hydraulically activated vacuum pump apparatus for an artificial limb, wherein the apparatus may comprise a housing, a first force receiving member configured to be received by the housing, with the first force receiving member having a first hydraulic surface, and the first hydraulic surface having a first force receiving member compressed position and a first force receiving member extended position. The apparatus may also include a second force receiving member configured to be received by the housing, wherein the second force receiving member may have a second hydraulic surface and a pneumatic surface, with the pneumatic surface having a second force receiving member compressed position and a second force receiving member extended position, and the pneumatic surface may be configured to draw air through an intake valve. In this case, the first hydraulic surface and the pneumatic surface may each have a larger surface area than the second hydraulic surface.

The apparatus may also comprise a hydraulic fluid hydraulically linking the first and second hydraulic surfaces, wherein linear displacement of the first hydraulic surface from the first force receiving member extended position to the first force receiving member compressed position is less than the linear displacement of the pneumatic surface from the second force receiving member extended position to the second force receiving member compressed position.

In this apparatus, the second force receiving member may be received by the first force receiving member. Furthermore, an outer perimeter of the second hydraulic surface may be greater than an outer perimeter of the pneumatic surface, or an outer perimeter of the second hydraulic surface may be less than an outer perimeter of the pneumatic surface.

The second hydraulic surface may intersect with a central axis of the second force receiving member. Displacement of the first force receiving member in a first direction may drive the second force receiving member in a second direction, with the first direction being opposite the second direction. The linear displacement of the first hydraulic surface may be between about 2 times smaller to about 10 times smaller than the linear displacement of the pneumatic surface. In some embodiments, the linear displacement of the first hydraulic surface may be between about 1.5 to about 10 times smaller or about 2 to about 10 times smaller than the linear displacement of the pneumatic surface.

In some embodiments, the intake valve may receive air from a socket configured to receive a residual limb.

According to yet another aspect of the present disclosure, a method of providing vacuum to an artificial limb socket is provided, comprising compressing a vacuum pump apparatus by driving a first piston into a first piston housing, the first piston having a first hydraulic surface hydraulically linked to a second hydraulic surface of a second piston, the first hydraulic surface having greater surface area than the second hydraulic surface, thereby driving displacement of the second piston to a greater displacement than the first piston, the displacement of the second piston withdrawing air from a socket of an artificial limb by expansion of a pneumatic chamber of the vacuum pump apparatus, wherein the linear expansion of the pneumatic chamber is greater than the linear movement of the first piston, and expanding the vacuum pump apparatus by withdrawing the first piston in the first piston housing, whereby the second piston expels air from the pneumatic chamber.

Another step of this method may include attaching the vacuum pump apparatus to the socket of the artificial limb. Additionally, compressing the vacuum pump apparatus comprises transferring body weight onto the artificial limb or bending the artificial limb. The second piston may be biased to expel air from the pneumatic chamber using a biasing member.

In some embodiments, a vacuum pump apparatus may be provided for prosthetic use. The apparatus may include a housing, a first force receiving member, and a second force receiving member. The first and second force receiving members may be configured to reciprocate within the housing. The second force receiving member may form a pneumatic chamber configured to receive air from a limb socket upon expansion and may be configured to evacuate air from the pump apparatus upon compression. In these embodiments, the second force receiving member may be positioned within the first force receiving member.

The above summary of the present invention is not intended to describe each embodiment or every implementation of the present invention. The Figures and the detailed description that follow more particularly exemplify a preferred embodiment.

BRIEF DESCRIPTION OF THE DRAWINGS

The accompanying drawings and figures illustrate a number of exemplary embodiments and are part of the specification. Together with the present description, these drawings demonstrate and explain various principles of this disclosure. A further understanding of the nature and advantages of the present invention may be realized by reference to the following drawings. In the appended figures, similar components or features may have the same reference label.

Figure 1A:
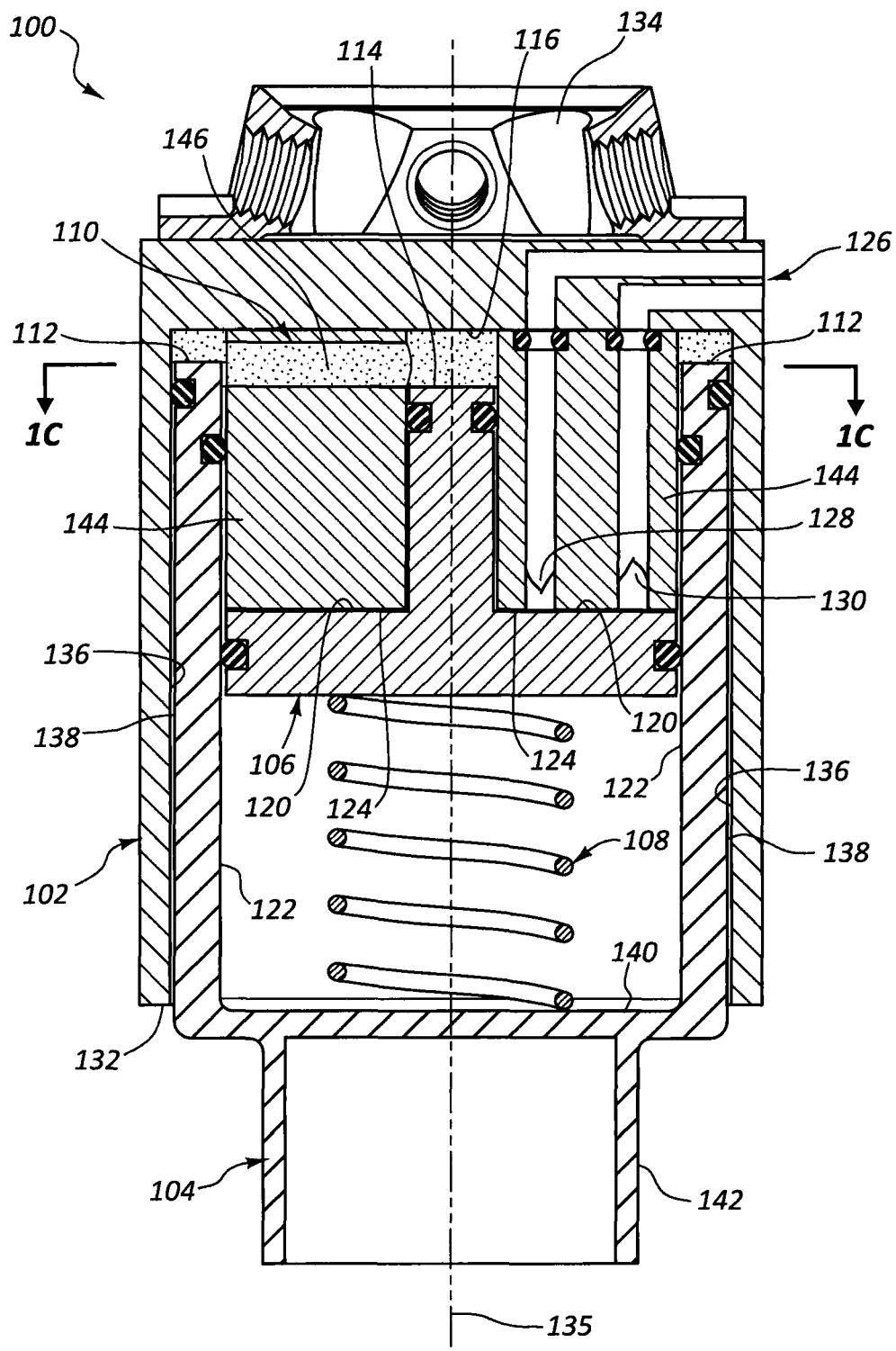
FIG. 1A is a side sectional view of a vacuum pump apparatus according to an embodiment of the present disclosure, with the pump apparatus in a fully extended position.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION

The design of prosthetic devices is typically driven by height, weight, cost and performance considerations. In general, taller prosthetic feet provide increased performance compared to shorter feet. Amputations occur at different locations on a limb, and a trade-off exists between residual limb length and the height available in the limb for prosthetic components. During the gait cycle, a significant moment is generated by the lever arm created by the prosthetic foot. A longer residual limb results in smaller reaction forces on the amputee's residual limb and therefore is more comfortable for the amputee. However, having more space available below the residual limb offers more space for interposition of prosthetic components. Vacuum suspension, when implemented correctly, may significantly improve performance for an amputee. Minimizing the amount of space taken by the vacuum pump may allow a larger variety of foot designs to be used. In cases where the amputee's residual limb is exceptionally long, there may not be enough space for a mechanical vacuum pump. Therefore pump height may be advantageously limited in an in-line vacuum pump.

One performance measure of a prosthetic vacuum pump is the rate of vacuum generation which is largely determined by the volume of air displaced in a single cycle of the vacuum pump. Therefore the vacuum generation rate may be advantageously increased in an in-line vacuum pump.

A mechanical vacuum pump may operate by pulling air from a target volume into a chamber and then expelling this air to the atmosphere. An in-line mechanical vacuum pump may be defined as a pump mounted "in-line" between the socket and the foot. Displacement of an in-line pump may reduce the length of the limb during compression of the pump and lengthen the limb during extension of the pump.

In-line vacuum pumps may also function as a shock absorber for a limb. Shock absorption typically increases comfort for the amputee, although significant change in length of an artificial leg during compression and extension of the pump can be a detriment. This shortening and lengthening characteristic of these limbs creates challenges, either with stubbing the toe during the swing phase of gait, having unequal leg length when standing with weight on both feet, or creating an unequal gait between right and left sides due to the shortening of the prosthetic leg. Strong, active amputees can cope with a change in limb length and such amputees tend to appreciate the advantages of shock absorption. Amputees who are less active tend to prefer a limb which minimizes the change in leg length during the gait cycle. Therefore, pumps designed for significant shock absorption are attractive for a portion of the amputee population, and pumps designed for minimal displacement are attractive for a different portion of the amputee population.

According to one aspect of the present disclosure, a mechanical pump is provided that may maximize the amount of air displaced in a single pump cycle (e.g., step) while minimizing the length change of the artificial limb. The mechanical pumps herein may also have reduced overall height. This may beneficially reduce the overall length of the pump portion of the limb to allow more space for other components.

While various embodiments of this disclosure are primarily directed to prosthetic legs, feet, sockets, and related devices, it is contemplated that the systems and apparatuses disclosed herein may be readily applied in other fields, such as orthotic devices, prostheses for other body parts, and related fields. Furthermore, it will be appreciated that the principles and elements of the present disclosure may be readily configured and applied in other settings.

Figure 1B:
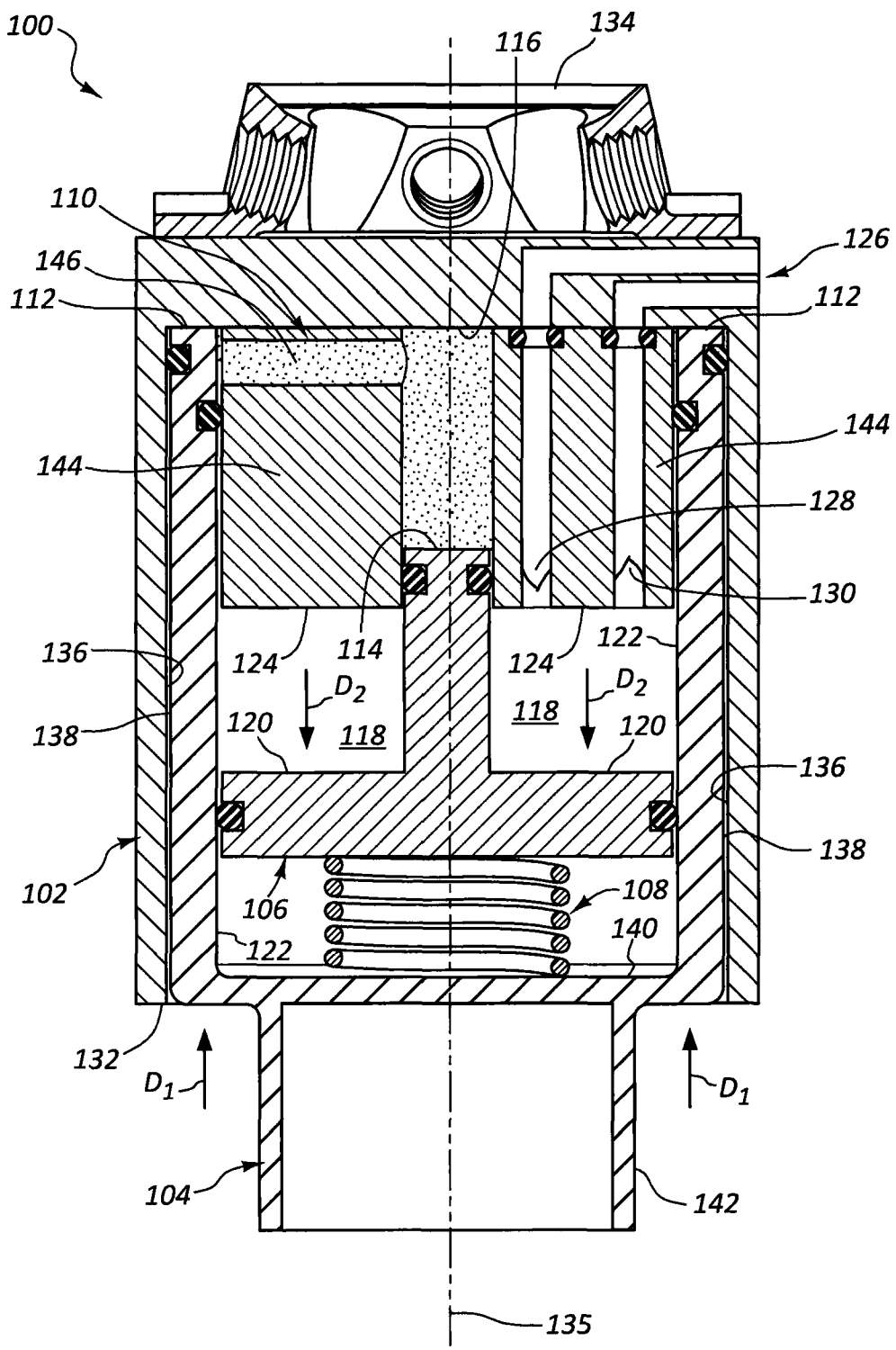
FIG. 1B is a side sectional view of the pump apparatus of FIG. 1A in a fully compressed position.
Figure 1C:
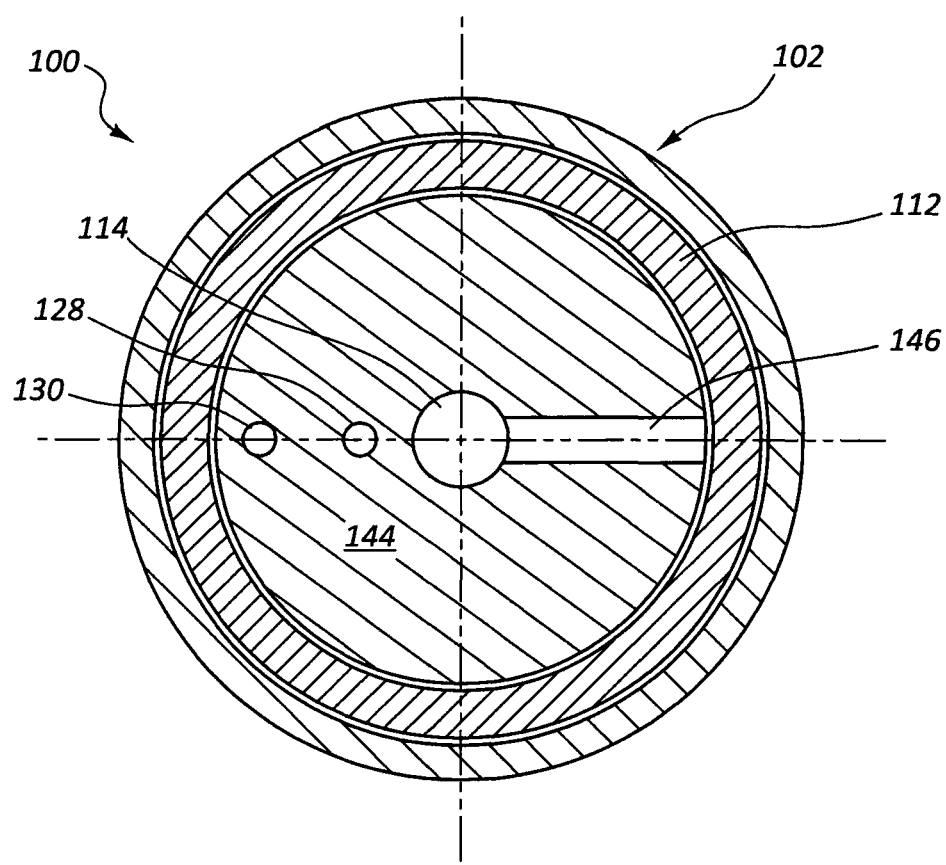
FIG. 1C is a top sectional view of the pump apparatus of FIG. 1A taken through lines 1C-1C in FIG. 1A.

Referring now to the figures in detail, FIGS. 1A-1C are views of an embodiment of a hydraulically amplified vacuum pump 100. FIGS. 1A-1B are side section views of the pump 100, and FIG. 1C is a top section view of the pump 100 taken through section lines 1C-1C in FIG. 1A. The views in FIGS. 1A-1B are views through a central plane of the pump 100, such as a sagittal plane.

The pump 100 may comprise a housing 102, an outer piston 104, and an inner piston 106. In some cases, the pistons 104, 106 may be referred to as force receiving members since they receive and transmit forces during the compression and expansion of the pump 100. Devices other than pistons may be implemented as force receiving members, such as hydraulically-linked members. The outer and inner pistons 104, 106 may be biased relatively away from each other by a spring element 108. A spring element 108 may comprise a coil spring or other type of elastic element or biasing element configured to be compressed and then to expand due to potential energy stored by the compression, such as, for example, a foam rubber member or elastic lattice. In some embodiments, the spring element 108 may not be present, such as when the housing 102 and outer piston 104 may be biased away from each other by gravity pulling the outer piston 104 from the housing 102. The spring element 108 does not necessarily have to press against the pneumatic piston, and alternate spring arrangements are possible, but if the spring element 108 presses against the piston it may minimize any tendency to cavitate the hydraulic fluid.

A hydraulic chamber 110 may be bounded by an outer piston hydraulic surface 112, an inner piston hydraulic surface 114, and an internal surface of the housing 116 facing the hydraulic chamber. The hydraulic chamber 110 may also be bounded by surfaces of a central column 144 of the housing 102. A pneumatic chamber 118 (see FIG. 1B) may be bounded by an inner piston pneumatic surface 120, an inner sidewall 122 of the outer piston 104, and a housing pneumatic surface 124. A valve assembly 126 is linked to the pneumatic chamber 118 that has at least an intake valve 128 and an exhaust valve 130. FIG. 1C also shows the position of these valves 128, 130 of the valve assembly 126.

The housing 102 of the pump 100 may be a generally hollow cylinder with an open end 132. In the configuration shown in FIGS. 1A-1C, the open end 132 is at the bottom of the housing 102, but the housing 102 may alternatively be inverted, with an open end 132 at the top of the housing 102 and the outer piston 104 emerging from the top end. The housing 102 may comprise an attachment portion 134 opposite the open end 132. In these figures, the attachment portion 134 is configured to receive a pyramid adapter of an artificial limb. Thus, it may be said that the housing has a socket connection portion since a pyramid adapter may connect to a socket or other socket-linked limb portion. Other attachment mechanisms or structures may be used in place of a pyramid adapter, however, as will be apparent to those having ordinary skill in the art and having the benefit of this disclosure.

Some embodiments may have a housing 102 that is integrally connected to another structure, such as integrally connected to the distal end of a limb socket or to a limb pylon. Typically, the pump 100 is positioned in-line with other components of the artificial limb or in-line with a prevailing force vector through the limb. A central longitudinal axis 135 may be defined running through the pump 100, along which axis 135 the outer and inner pistons 104, 106 and housing 102 may each translate relative to each other. The central longitudinal axis 135 may intersect the inner piston hydraulic surface 114 and a plane defined by the outer piston hydraulic surface 112 or inner piston pneumatic surface 120.

The housing 102 and pistons 104, 106 may beneficially comprise a metal, polymer, or composite construction that has strength and durability while subjected to the pressures and rigors applied when they are used as part of an artificial limb. Thus, for example, an inner sidewall 136 of the housing 102 may have a smooth, consistent finish capable of a sealing interface with an outer surface 138 of the outer piston 104 without deformation of the inner sidewall 136 while the pump 100 is reoriented or the outer piston 104 is subjected to lateral forces.

As shown in FIGS. 1A-1B, the interface between the outer surface 138 and inner sidewall 136 may be sealed by an o-ring or other resilient seal. Similarly, o-rings or other seals may be used at the inner sidewall 122 of the outer piston, adjacent to the inner piston hydraulic surface 114, adjacent to the inner piston pneumatic surface 120, and anywhere else in the pump 100 needed to preserve pressure and fluid retention for the pneumatic chamber 118 or hydraulic chamber 110.

The outer piston 104 may be generally cylindrical and may have a generally cylindrical inner bore defined by the inner sidewall 122 and an end surface 140. This inner bore of the outer piston 104 may be sized to sealingly receive the outer circumference of the inner piston pneumatic surface 120 and a column 144 of the housing 102 that includes the valve assembly 126. The column 144 may be an inner block of the housing configured to sealingly engage the inner and/or outer pistons 104, 106 and provide a hydraulic channel 146 linking the inner piston and outer piston hydraulic surfaces 112, 114. The column 144 may be integrated with the rest of the housing 102 as a single piece, or may be attachable to the interior of the housing 102, such as at internal surface 116. In some embodiments, the internal surface 116 is defined by the housing 102 and by the column 144, such as, for example, by being defined at least in part by the internal surface of a hydraulic channel 146.

The pump 100 may operate as follows. Starting in the position of FIG. 1A, as the outer piston 104 translates along the central longitudinal axis 135, such as in response to a wearer placing weight on the pump 100 while wearing an artificial limb, the outer piston hydraulic surface 112 is driven into the housing 102 (away from the open end 132), thereby displacing hydraulic fluid in the hydraulic chamber 110. This movement may be in direction $D_1$, which is indicated in FIG. 1B. This movement causes the hydraulic fluid to pass from the area adjacent to the outer piston hydraulic surface 112 through the hydraulic channel 146 and toward the inner piston hydraulic surface 114. This makes the inner piston hydraulic surface 114 move toward the open end 132 of the housing 102 in direction $D_2$, compressing the spring element 108 and generating negative pressure in the pneumatic chamber 118, as shown in FIG. 1B. The movement of the inner piston pneumatic surface 120 thus generates vacuum in the pneumatic chamber 118 and draws air into the pneumatic chamber 118 through the intake valve 128.

Thus, the intake valve 128 may be linked the a socket by an intake line or tube. The intake valve may be beneficially connected to a socket of an artificial limb so that the intake of air to the pneumatic chamber 118 generates vacuum in the socket. See, e.g., FIG. 1D.

When force on the outer piston 104 is removed, the spring element 108 may help to drive the inner piston 106 to decrease the volume of the pneumatic chamber 118 by expelling air through the exhaust valve 130. This motion may also drive the inner piston hydraulic surface 114 so that hydraulic fluid passes again through the hydraulic channel 146 and drives the outer piston 104 outward relative to the open end 132 of the housing 102 (opposite direction $D_1$) until returning to the position of FIG. 1A. In this manner, the outer piston 104 may be said to reciprocate within the housing 102 and the inner piston 106 may be said to reciprocate within the outer piston 104.

This mechanical action of the pump 100 may allow an artificial limb to efficiently evacuate air from a limb socket or other component with minimal deflection of the pump 100 in each step or cycle of the outer piston 104. In some exemplary embodiments, the linear displacement of the outer piston hydraulic surface 112 along the central longitudinal axis 135 may be about 1 millimeter and the corresponding linear displacement of the inner piston hydraulic surface 114 along the central axis 135 may be about 30 millimeters. Thus, for about 1 millimeter of displacement of the outer piston 104, the inner piston 106 may displace about 30 millimeters. This means the inner piston pneumatic surface 120 also displaces about 30 times as much as the outer piston 104. In some embodiments, about ten times as much displacement is achieved. In general, an input displacement of n millimeters may result in a piston movement of n times the ratio of the outer piston hydraulic surface 112 to the inner piston hydraulic surface 114.

Because the surface area of the inner piston pneumatic surface 120 is much greater than the surface area of the inner piston hydraulic surface 114, the volume of air drawn into the pneumatic chamber 118 is much greater than the volume of hydraulic fluid needed to displace the inner piston hydraulic surface 114 toward the spring element 108. Thus, significant vacuum may be generated per cycle of the pump 100 (e.g., per step) with minor displacement and compression of the exterior of the pump 100 as a whole.

One feature of the pump 100 that helps produce this efficient vacuum generation is the proportional sizes of the surface areas of the outer piston hydraulic surface 112 and the inner piston hydraulic surface 114. The outer piston hydraulic surface 112 extends around the entire end of the outer piston 104, so its surface area is significantly larger than the surface area of the inner piston hydraulic surface 114. See FIG. 1C. Thus, due to the hydraulic connection between these surfaces 112, 114, small displacement of the outer piston 104 produces large displacement of the inner piston 106.

A small amount of displacement of the outer piston 104 (e.g., about 4 millimeters or less) may be beneficial for an in-line pump of an artificial limb since the compression may act as a minor source of shock absorption and may therefore improve comfort and utility of the limb for the wearer while minimizing the effects of an uneven gait. Furthermore, the compact design of the pump 100 means it may be used with a large variety of limbs without being too long or restricting the use of the pump 100 with other tall components. The pump's generally low number of parts may also help to increase reliability and decrease maintenance requirements of the pump 100. In just a few cycles of the pump 100, a significant amount of air may be displaced, so the time needed to achieve a desirable vacuum level in a socket may be short.

The end of the outer piston 104 opposite the attachment portion 134 of the housing 102 may comprise an attachment feature 142. The attachment feature 142 may be configured to attach to or receive a pylon of an artificial limb, such as a shin portion of an artificial foot. In some embodiments, the attachment feature 142 may be a pyramid adapter or may be configured to receive a pyramid adapter, similar to attachment portion 134.

Figure 1D:
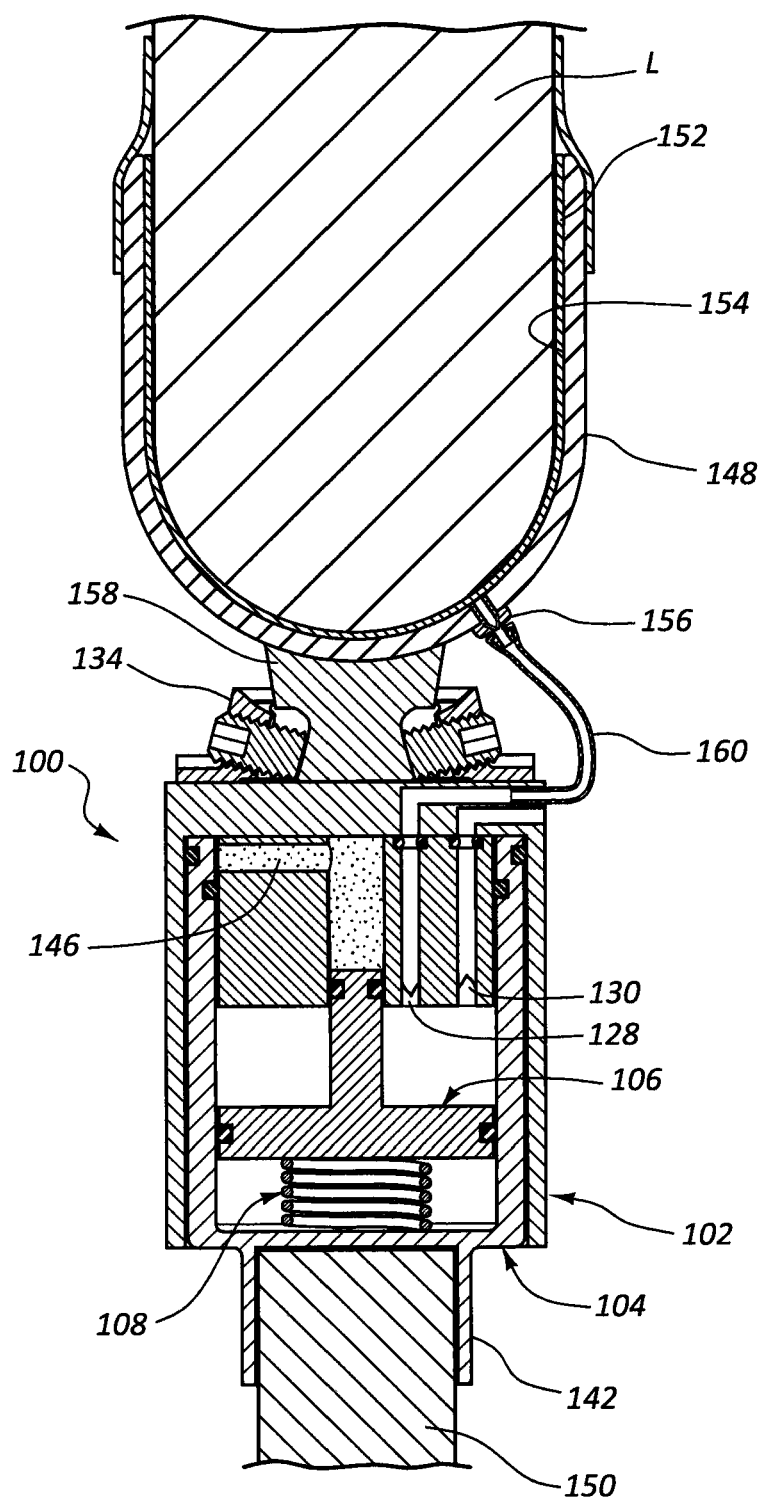
FIG. 1D is a side sectional view of the pump apparatus of FIG. 1A attached to a residual limb socket and a pylon in an exemplary limb configuration.

FIG. 1D shows a side profile section view of a pump 100 attached to a limb socket 148 and a pylon 150. The limb socket 148 may be configured to receive and sealingly retain a residual limb L. The limb L may be inserted into the limb socket 148 while covered with a liner 152, sock, or other interposed covering material. The liner 152 may be used to help prevent air from escaping the socket 148 due to comprising a generally flexible sealing material when brought into contact with the inner surface 154 of the socket 148. The liner 152 may also reduce irritation of the residual limb L and facilitate the insertion and removal of the limb L from the socket 148. A liner 152 may extend up the residual limb and a sleeve may cover a portion of the residual limb, liner, and socket to seal the system.

The socket 148 may also include a vacuum valve 156 linked to the intake valve 128 of the pump 100 and a distally-positioned pyramid adapter 158 connected to the attachment portion 134 of the housing 102. With the vacuum valve 156 linked to the socket 148, air may be withdrawn from the interior of the socket 148 through a vacuum line 160 as the pump 100 reciprocates in the manner described above.

The pylon 150 may link the pump 100 to an artificial limb, such as a shin portion, femoral portion, or ankle portion. Thus, the pump 100 may be used in a variety of different lengths of artificial limbs and in a variety of positions in the artificial limbs.

Figure 2A:
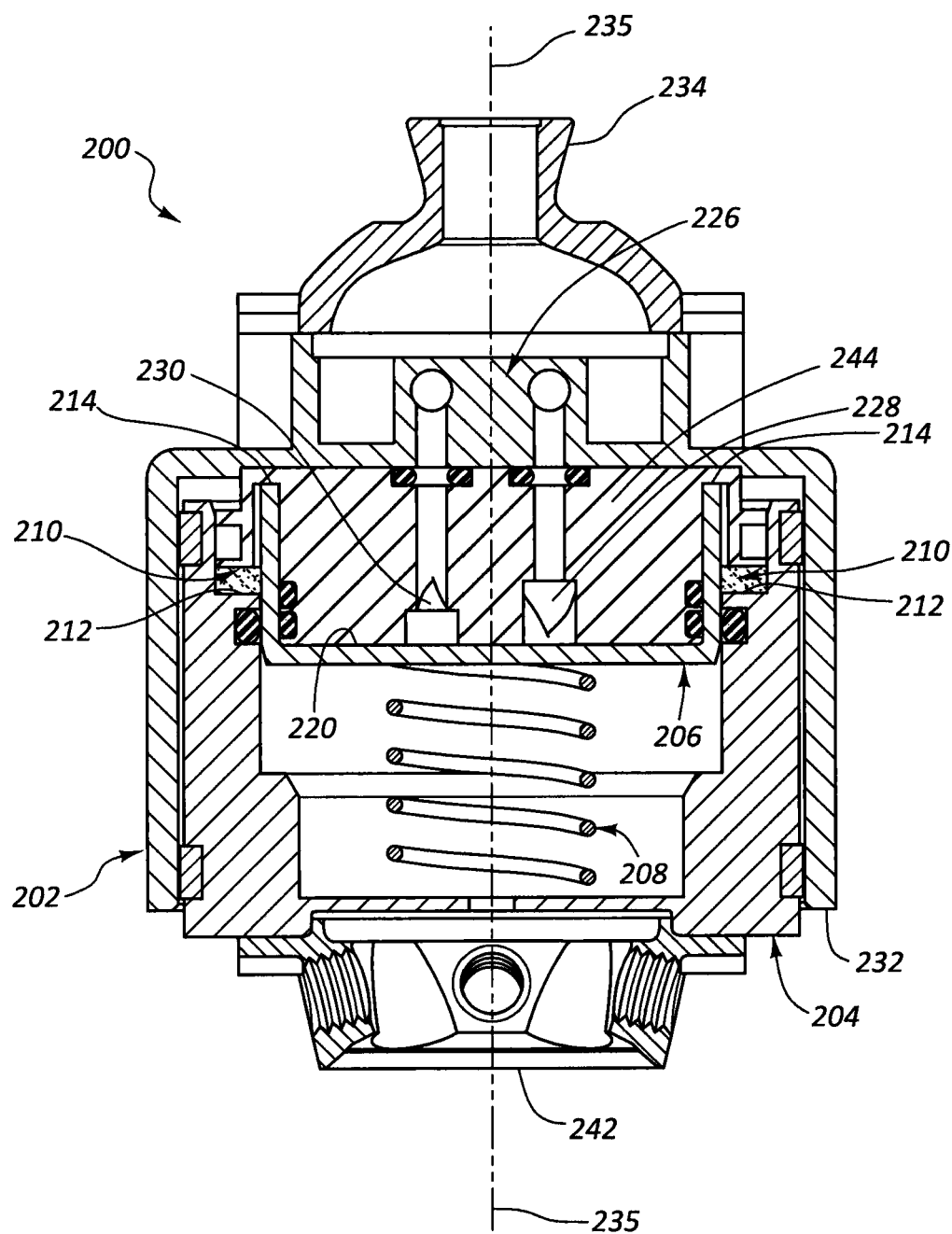
FIG. 2A is a side sectional view of a vacuum pump apparatus according to another embodiment of the present disclosure, with the pump apparatus in a fully extended position.
Figure 2B:
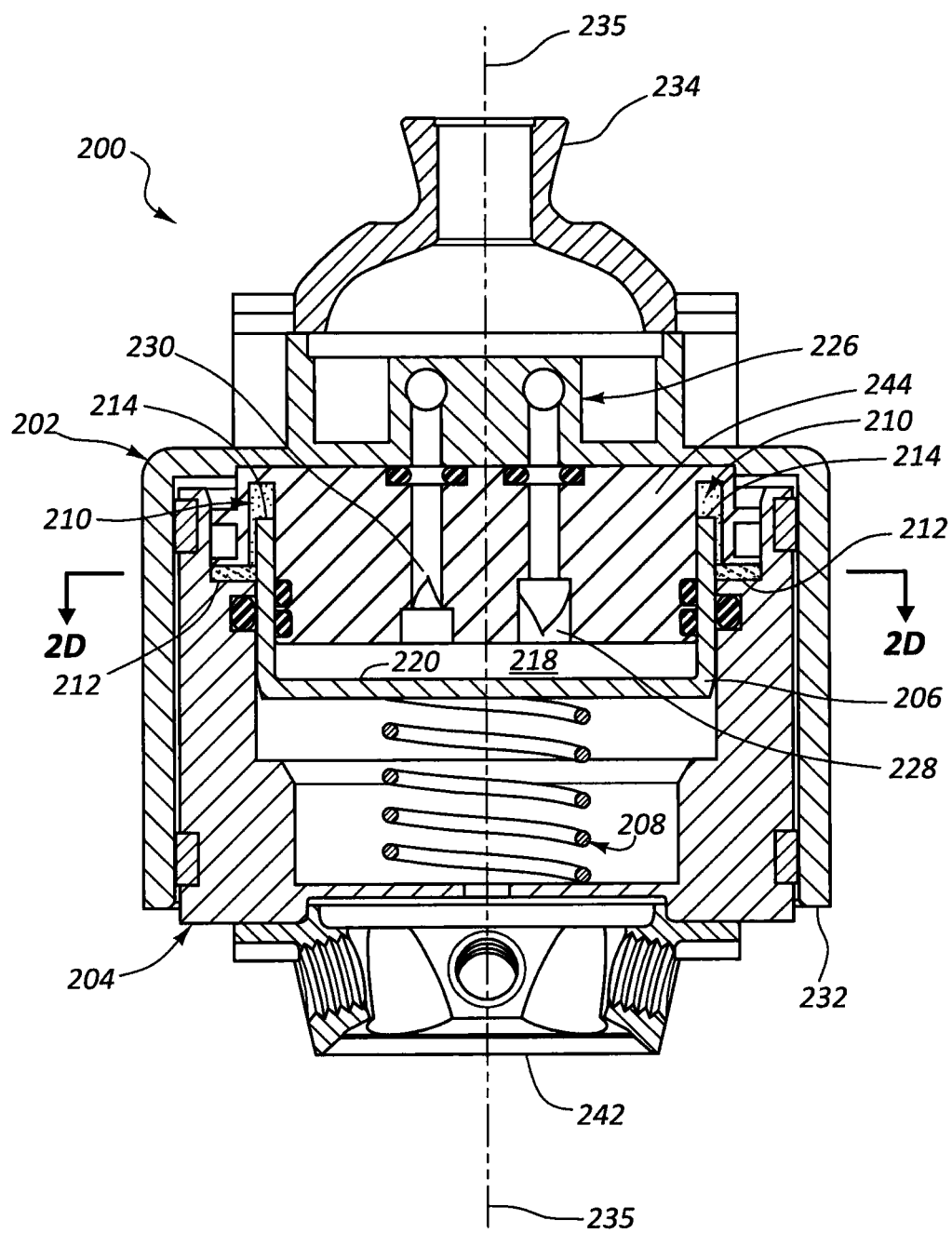
FIG. 2B is a side sectional view of the pump apparatus of FIG. 2A in a mid-stroke position.
Figure 2C:
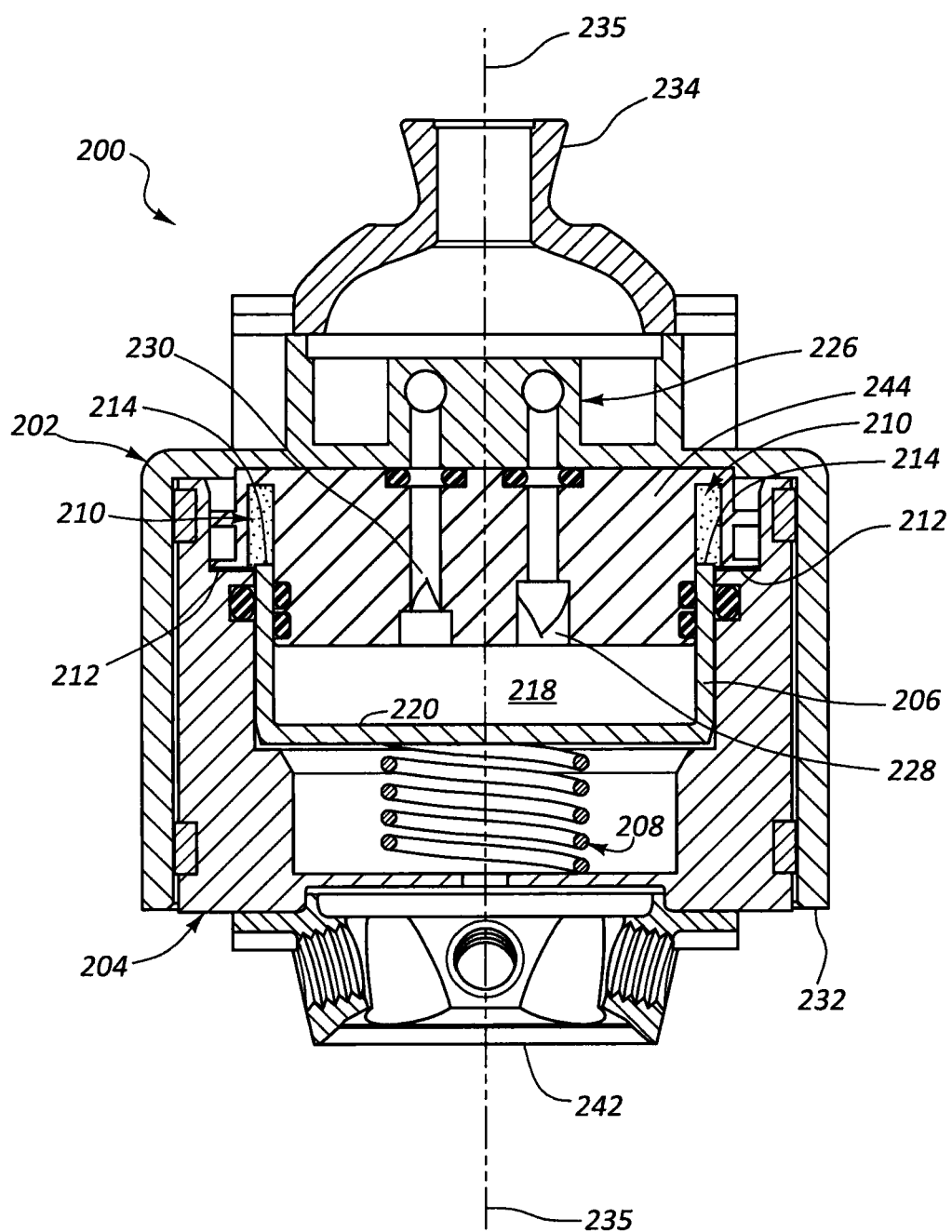
FIG. 2C is a side sectional view of the pump apparatus of FIG. 2A in a fully compressed position.
Figure 2D:
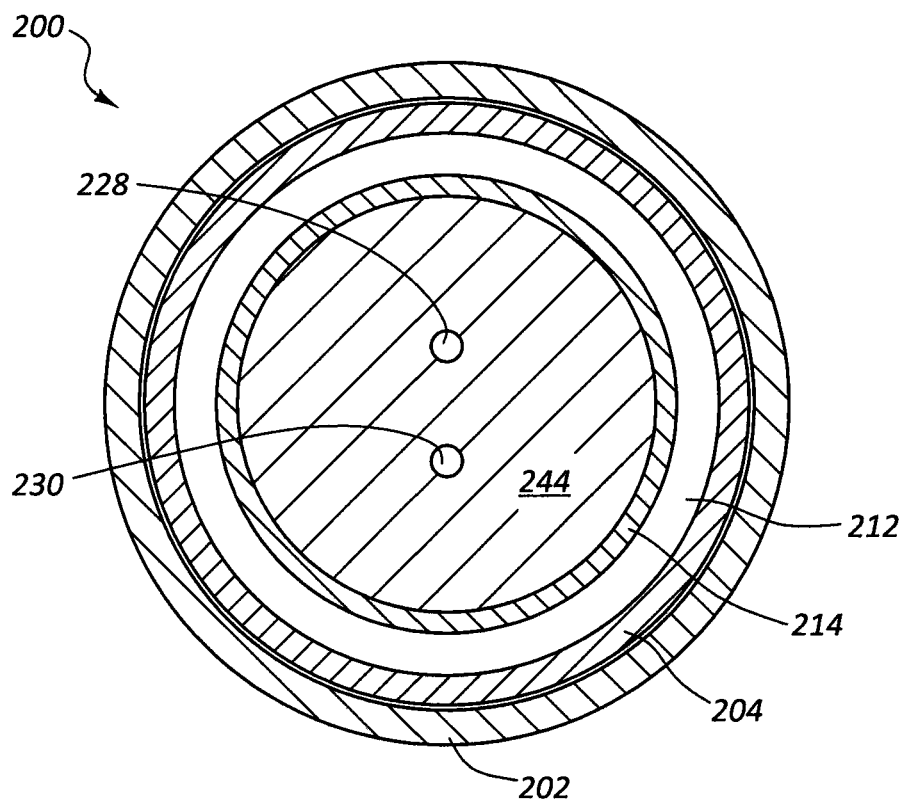
FIG. 2D is a top sectional view of the pump apparatus of FIG. 2A taken through lines 2D-2D in FIG. 2B.

FIGS. 2A-2D show another embodiment of a pump 200 for a prosthetic or orthotic device. FIG. 2A shows a section view of the pump 200 at full extension, and FIGS. 2B and 2C show section views of the pump 200 at mid-stroke and fully compressed, respectively. FIG. 2D is a section view of the pump 200 in the position of FIG. 2B, with the section taken through section lines 2C-2C. The pump 200 comprises a housing 202, outer piston 204, inner piston 206, and spring element 208 similar to the pump 100 of FIGS. 1A-1C. The pump 200 has a hydraulic chamber 210 defined in part by the housing 202, an outer piston hydraulic surface 212 and an inner piston hydraulic surface 214. A pneumatic chamber 218 is formed by the inner piston 206 and a column 244 of the housing 202 within the inner piston 206. A valve assembly 226 is disposed in the column 244 and housing 202 that may comprise an intake valve 228 and exhaust valve 230. Again, in some embodiments the spring element 208 may be omitted, such as when gravity is used to bias the housing 202 and outer piston 204 apart.

Similar to pump 100, the housing 202 has an open end 232 and an attachment portion 234. In this embodiment, the attachment portion 234 is a pyramid adapter. The outer piston 204 also includes an attachment feature 242. Here, the attachment feature 242 is configured to receive a pyramid adapter, similar to attachment portion 134.

As the outer piston 204 moves along a central longitudinal axis 235 of the pump 200 from the position of FIG. 2A to the position of FIG. 2B, the outer piston hydraulic surface 212 moves away from the open end 232 of the housing 202 and hydraulically drives the inner piston hydraulic surface 214 toward the open end 232. Driving the inner piston 206 in this direction draws an inner piston pneumatic surface 220 away from the column 244, thereby expanding the pneumatic chamber 218 (see FIG. 2B). Due to the sealing connection between the inner piston 204 and the column 244, negative pressure may be generated in the pneumatic chamber and the inner piston 204 draws air through the intake valve 228 to fill the pneumatic chamber. The intake valve 228 may thus draw air from a socket of an artificial limb upon compression of the outer piston 204 into the housing 202. The intake and exhaust valves 228, 230 may therefore be one-way valves to prevent air from the pneumatic chamber 218 from leaking into a connected socket and to prevent ambient air from being drawn into the pneumatic chamber 218 instead of the pneumatic chamber 218 being filled with air from the socket.

At full compression of the pump 200, as shown in FIG. 2C, the pneumatic chamber 218 is at maximum volume. By releasing pressure on the outer piston 204, the spring element 208 drives the inner piston 206 toward the column 244, and the air in the chamber 218 is driven through the exhaust valve 230 and out of the pump 200. Simultaneously, the outer piston 204 is hydraulically driven by the inner piston hydraulic surface 214 so that it moves toward the open end 232 to reach the position of FIG. 2B. This process may therefore be cyclical, such as occurring with a walking gait cycle of the amputee wearing the pump 200.

The pump 200 operates similar to pump 100 in many ways, but instead of having a central column to support the inner piston 206 and a channel 146 for hydraulic fluid, the inner piston hydraulic surface 214 is instead located circumferentially on the inner piston 206. Thus, the inner piston hydraulic surface 214 is positioned radially outward from the inner piston pneumatic surface 220 rather than being located radially inward relative to the outer circumference of the inner piston pneumatic surface 120, as in pump 100. See FIG. 2D. The inner piston hydraulic surface 214 still, however, has much less surface area than the inner piston pneumatic surface 220 so that the hydraulics of the pump 200 may displace a large volume of air in the pneumatic chamber 218 in response to a relatively small displacement of hydraulic fluid between the housing 202 and the inner piston hydraulic surface 214. As shown in FIGS. 2A-2C, the linear displacement of the inner piston hydraulic surface 214 is the same as the displacement of the inner piston pneumatic surface 220 along the central longitudinal axis 235 between FIGS. 2A and 2C, but because the surface area of the inner piston hydraulic surface 214 is much smaller than the surface area of the inner piston pneumatic surface 220, the volumetric displacement is significantly larger for the inner piston pneumatic surface 220.

In some example embodiments, a total displacement of about 3 millimeters of the outer piston 204 may produce a total displacement of about 10 millimeters of the inner piston 206. Thus, it may be said that a ratio of displacement of a first piston to displacement of a second piston may be about 3 to 1. In other embodiments, this ratio may be greater, such as about 10 to 1. In some arrangements the surface areas of the inner and outer hydraulic surfaces 212, 214 may be changed according to design needs to increase or decrease the ratio of displacement of each piston 204, 206. For example, in some cases the displacement of the outer piston 204 may be desirably larger than three millimeters to provide greater shock absorption capability to the pump 200, so the surface area of the outer piston hydraulic surface 212 may be designed with decreased area so that more hydraulic displacement is required to produce the same movement of hydraulic fluid in the hydraulic chamber 210.

FIG. 2D may be helpful to compare the relative surface areas of the inner piston hydraulic surface 214 and the inner piston pneumatic surface 220 (which is immediately behind the column 244 in this view). From this perspective, the inner piston hydraulic surface 214 is a ring around the inner piston pneumatic surface 220 that does not overlap with the outer circumference of the inner piston pneumatic surface 220. The outer piston hydraulic surface 212 may also be compared to the inner piston hydraulic surface 214 in this view, which shows that the surface area of surface 212 is considerably larger than the surface area of surface 214. Again, this means that each increment of displacement of the outer piston hydraulic surface 212 will hydraulically produce a greater increment of displacement of the inner piston hydraulic surface 214. Thus, the pump 200 may provide reduced overall compression between fully extended and fully compressed positions while still improving the volume of air displaced within the pneumatic chamber 218 as compared to traditional mechanical pump systems.

The pump 200 may also be advantageous in the alternative to pump 100 because it may allow alternative intake and exhaust valve placement that runs about centrally through the column 244 instead of through a side portion of the column 244. It further eliminates the need for the hydraulic channel 146, which may decrease manufacturing costs and allow for easier maintenance and cleaning of the pump 200. Each pump 100, 200, however, may find use in a variety of settings according to the needs of each prosthetist or amputee.

While the hydraulic chambers 110, 210 may beneficially be filled with hydraulic fluid, it will be appreciated that in some embodiments a non-hydraulic fluid such as, for example, a gas (e.g., air) may be used. Thus, in some cases these chambers 110, 210 may operate pneumatically instead of hydraulically.

While reference herein has generally been made to use of a pump for socketed prostheses for amputees, it will be appreciated that the principles and elements of the present disclosure are generally applicable to orthotic devices and devices configured for wearers who may not be amputees, such as individuals with amelia, meromelia, and other limb disorders.

In another aspect of the present disclosure, a method of providing vacuum to an artificial limb socket is provided that minimizes limb or pump displacement. The method may comprise compressing a vacuum pump apparatus by driving a first piston into a first piston housing, wherein the first piston has a first hydraulic surface hydraulically linked to a second hydraulic surface of a second piston and the first hydraulic surface has greater surface area than the second hydraulic surface. This drives displacement of the second piston to a greater displacement than the first piston. The displacement of the second piston may withdraw air from a socket of an artificial limb by expansion of a pneumatic chamber of the vacuum pump apparatus. In this embodiment, linear expansion of the pneumatic chamber is greater than the linear movement of the first piston. The method may further comprise expanding the vacuum pump apparatus by withdrawing the first piston in the first piston housing, whereby the second piston expels air from the pneumatic chamber.

The vacuum pump apparatus may also be attached to the socket of the artificial limb. Compressing the vacuum pump may comprise transferring body weight onto the artificial limb or bending of the artificial limb. Thus, the vacuum pump apparatus may be configured to drive the pistons upon bending of a limb, such as bending of a knee or elbow. A linkage to a housing (e.g., housing 102) and to a piston (e.g., outer piston 104) may be necessary to ensure proper displacement of the pump apparatus while being used in a bend-activated configuration.

In another embodiment, the method may include biasing the second piston to expel air from the pneumatic chamber using an elastic element or biasing member. The biasing member may be a spring element (e.g., spring element 108) or another biasing device.

Various inventions have been described herein with reference to certain specific embodiments and examples. However, they will be recognized by those skilled in the art that many variations are possible without departing from the scope and spirit of the inventions disclosed herein, in that those inventions set forth in the claims below are intended to cover all variations and modifications of the inventions disclosed without departing from the spirit of the inventions. The terms "including:" and "having" come as used in the specification and claims shall have the same meaning as the term "comprising."

What is claimed is:

1. A vacuum pump apparatus for prosthetic use, the apparatus comprising:
    a housing having a socket connection portion, an inlet, an outlet, and an inner surface, the socket connection portion being adapted to connect to a prosthetic socket;
    a first force receiving member configured to reciprocate within the housing, the first force receiving member comprising an artificial limb connection portion, the artificial limb connection portion being adapted to connect to an artificial limb portion;
    a second force receiving member configured to reciprocate within the housing, the second force receiving member having a pneumatic surface, a pneumatic chamber being formed at least in part between the pneumatic surface and the inner surface of the housing, the pneumatic chamber configured to receive air from the prosthetic socket through the housing inlet upon expansion of the pneumatic chamber and configured to evacuate air from the pump apparatus through the housing outlet upon compression of the pneumatic chamber, the second force receiving member being positioned within the first force receiving member;
    a hydraulic fluid positioned between the housing, the first force receiving member, and second force receiving member, and displacement of the first force receiving member relative to the housing displaces the hydraulic fluid to move the second force receiving member relative to the housing.

2. A vacuum socket pump apparatus for an artificial limb, the pump apparatus comprising:
    a limb socket;
    a housing having a socket connection portion, an inlet and an outlet, the socket connection portion being adapted to connect to the limb socket;
    a first piston configured to reciprocate within the housing, the first piston comprising an artificial limb connection portion, the artificial limb connection portion being adapted to connect to an artificial limb portion;
    a second piston configured to reciprocate within the first piston upon displacement of the first piston relative to the housing, the second piston having a pneumatic surface, the second piston and the housing forming a pneumatic chamber between an interior surface of the housing and the pneumatic surface;
    a vacuum pathway providing fluid communication between the limb socket and the pneumatic chamber via the housing inlet;
    a hydraulic fluid positioned between the housing, the first piston, and the second piston;

wherein the pneumatic chamber is configured to receive air from the socket through the vacuum pathway upon expansion of the pneumatic chamber and to evacuate air from the pump apparatus through the housing outlet upon compression of the pneumatic chamber;

wherein displacement of the first piston relative to the housing displaces the hydraulic fluid to move the second piston relative to the housing.

3. The vacuum socket pump apparatus of claim 2, wherein the first piston has a first hydraulic surface and the second piston has a second hydraulic surface, and the first hydraulic surface has a greater surface area than the second hydraulic surface.

4. The vacuum socket pump apparatus of claim 3, wherein the pneumatic surface has a greater surface area than the second hydraulic surface.

5. The vacuum socket pump apparatus of claim 2, wherein the second piston is biased away from the first piston by a biasing member.

6. The vacuum socket pump apparatus of claim 2, further comprising an intake valve and an exhaust valve, the intake valve providing one-way displacement of air from the socket into the pneumatic chamber, the exhaust valve providing one-way displacement of air out of the pneumatic chamber.

7. The vacuum socket pump apparatus of claim 2, wherein the socket connection portion comprises a pyramid connector interface or the artificial limb connection portion comprises a pyramid connector interface.

8. The vacuum socket pump apparatus of claim 2, wherein the artificial limb is part of, or entirely, an artificial leg.

9. The vacuum socket pump apparatus of claim 8, wherein the vacuum pump apparatus is positioned in a shin portion of the artificial leg.

10. The vacuum socket pump apparatus of claim 8, wherein the vacuum pump apparatus is positioned in a femoral portion of the artificial leg.

11. The vacuum socket pump apparatus of claim 2, wherein the displacement of the first piston relative to the housing between a fully extended position and a fully compressed position is about 10 millimeters or less.

12. The vacuum socket pump apparatus of claim 2, wherein displacement of the first piston in a first direction relative to the housing displaces the hydraulic fluid to move the second piston in a second direction relative to the housing, the second direction being opposite the first direction.

13. A hydraulically activated vacuum pump apparatus for an artificial limb, the apparatus comprising:
    a housing;
    a first force receiving member configured to be received by the housing, the first force receiving member having a first hydraulic surface, the first hydraulic surface having a first force receiving member compressed position and a first force receiving member extended position;
    a second force receiving member configured to be received by the housing, the second force receiving member having a second hydraulic surface and a pneumatic surface, the pneumatic surface having a second force receiving member compressed position and a second force receiving member extended position, the pneumatic surface configured to draw air through an intake valve, the first hydraulic surface and the pneumatic surface each having a larger surface area than the second hydraulic surface;
    a hydraulic fluid hydraulically linking the first and second hydraulic surfaces;
    wherein linear displacement of the first hydraulic surface from the first force receiving member extended position to the first force receiving member compressed position is less than linear displacement of the pneumatic surface from the second force receiving member extended position to the second force receiving member compressed position.

14. The apparatus of claim 13, wherein the second force receiving member is received by the first force receiving member.

15. The apparatus of claim 13, wherein an outer perimeter of the second hydraulic surface is greater than an outer perimeter of the pneumatic surface.

16. The apparatus of claim 13, wherein an outer perimeter of the second hydraulic surface is less than an outer perimeter of the pneumatic surface.

17. The apparatus of claim 13, wherein the second hydraulic surface intersects with a central axis of the second force receiving member.

18. The apparatus of claim 13, wherein displacement of the first force receiving member in a first direction drives the second force receiving member in a second direction, the first direction being opposite the second direction.

19. The apparatus of claim 13, wherein the intake valve is configured to receive air from a portion of the artificial limb.

20. The apparatus of claim 19, wherein the portion of the artificial limb is a socket configured to receive a residual limb.

21. The apparatus of claim 13, wherein the linear displacement of the first hydraulic surface is between 2 times smaller to 10 times smaller than the linear displacement of the pneumatic surface.

* * * * *